United States Patent [19]

Bruneau

[11] Patent Number: 5,240,941
[45] Date of Patent: Aug. 31, 1993

[54] THIOXO QUINOLINE COMPOUNDS, COMPOSITION AND METHOD OF USE

[75] Inventor: Pierre A. R. Bruneau, Ludes, France

[73] Assignees: ICI Pharma, Cergy Cedex, France; Imperial Chemical Industries PLC, London, England

[21] Appl. No.: 728,371

[22] Filed: Jul. 11, 1991

[30] Foreign Application Priority Data

Jul. 13, 1990 [EP] European Pat. Off. ............ 90402034
Jan. 15, 1991 [EP] European Pat. Off. ............ 91400079

[51] Int. Cl.$^5$ .................... A61K 31/47; C07D 215/36
[52] U.S. Cl. .................... 514/312; 544/284; 544/285; 544/286; 544/287; 546/141; 546/142; 546/155; 546/157; 546/158
[58] Field of Search .................... 546/155, 157, 158; 514/312

[56] References Cited

U.S. PATENT DOCUMENTS

| | | | |
|---|---|---|---|
| 3,661,917 | 5/1972 | Kaiser et al. | 260/293.73 |
| 3,743,737 | 7/1973 | Kaiser et al. | 424/267 |
| 4,876,346 | 10/1989 | Musser et al. | 546/172 |
| 4,918,081 | 4/1990 | Huang et al. | 514/311 |
| 4,920,130 | 4/1990 | Huang et al. | 514/311 |
| 4,920,131 | 4/1990 | Huang et al. | 514/311 |
| 4,920,132 | 4/1990 | Huang et al. | 514/314 |
| 4,920,133 | 4/1990 | Huang et al. | 514/314 |

FOREIGN PATENT DOCUMENTS

| | | |
|---|---|---|
| 0110405 | 6/1984 | European Pat. Off. . |
| 0181568 | 5/1986 | European Pat. Off. . |
| 0200101 | 12/1986 | European Pat. Off. . |
| 0271287 | 6/1988 | European Pat. Off. . |
| 0349062 | 6/1989 | European Pat. Off. . |

Primary Examiner—C. Warren Ivy
Assistant Examiner—James H. Turnipseed
Attorney, Agent, or Firm—Cushman, Darby & Cushman

[57] ABSTRACT

The invention concerns a thioxo heterocycle of the formula I

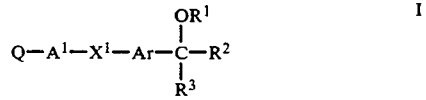

wherein Q is a 10-membered bicyclic heterocyclic moiety containing 1 or 2 N's which bears 1 or 2 thioxo substituents and which is optionally further substituted;
$A^1$ is a direct link to $X^1$ or (1-3C)alkylene;
$X^1$ is oxy, thio, sulphinyl, sulphonyl or imino;
Ar is optionally substituted phenylene or pyridylene;
$R^1$ is (1-4C)alkyl, (3-4C)alkenyl or (3-4C)alkynyl; and
$R^2$ and $R^3$ together form a group of the formula $-A^2-X^2-A^3-$ which, together with the carbon atom to which $A^2$ and $A^3$ are attached, defines a ring having 5 to 7 ring atoms, wherein each of $A^2$ and $A^3$ is (1-3C)alkylene and $X^2$ is oxy, thio, sulphinyl or sulphonyl;
or a pharmaceutically-acceptable salt thereof.

The compounds of the invention are inhibitors of the enzyme 5-lipoxygenase.

9 Claims, No Drawings

THIOXO QUINOLINE COMPOUNDS, COMPOSITION AND METHOD OF USE

This invention concerns novel thioxo heterocycles and more particularly novel thioxo heterocycles which are inhibitors of the enzyme 5-lipoxygenase (hereinafter referred to as 5-LO). The invention also concerns processes for the manufacture of said thioxo heterocycles and novel pharmaceutical compositions containing them. Also included in the invention is the use of said thioxo heterocycles in the treatment of various inflammatory and/or allergic diseases in which the direct or indirect products of 5-LO catalysed oxidation of arachidonic acid are involved, and the production of new medicaments for such use.

As stated above the thioxo heterocycles described hereinafter are inhibitors of 5-LO, which enzyme is known to be involved in catalysing the oxidation of arachidonic acid to give rise via a cascade process to the physiologically active leukotrienes such as leukotriene $B_4$ ($LTB_4$) and the peptido-lipid leukotrienes such as leukotriene $C_4$ ($LTC_4$) and leukotriene $D_4$ ($LTD_4$) and various metabolites.

The biosynthetic relationship and physiological properties of the leukotrienes are summarised by G. W. Taylor and S. R. Clarke in *Trends in Pharmacological Sciences*, 1986, 7, 100–103. The leukotrienes and their metabolites have been implicated in the production and development of various inflammatory and allergic diseases such as inflammation of the joints (especially rheumatoid arthritis, osteoarthritis and gout), inflammation of the gastrointestinal tract (especially inflammatory bowel disease, ulcerative colitis and gastritis), skin disease (especially psoriasis, eczema and dermatitis) and respiratory disease (especially asthma, bronchitis and allergic rhinitis), and in the production and development of various cardiovascular and cerebrovascular disorders such as myocardial infarction, angina and peripheral vascular disease. In addition the leukotrienes are mediators of inflammatory diseases by virtue of their ability to modulate lymphocyte and leukocyte function. Other physiologically active metabolites of arachidonic acid, such as the prostaglandins and thromboxanes, arise via the action of the enzyme cyclooxygenase on arachidonic acid.

We have now discovered that certain thioxo heterocycles are effective as inhibitors of the enzyme 5-LO and thus of leukotriene biosyntheses. Thus, such compounds are of value as therapeutic agents in the treatment of, for example, allergic conditions, psoriasis, asthma, cardiovascular and cerebrovascular disorders, and/or inflammatory and arthritic conditions, mediated alone or in part by one or more leukotrienes.

According to the invention there is provided a thioxo heterocycle of the formula I (set out hereinafter) wherein Q is a 10-membered bicyclic heterocyclic moiety containing one or two nitrogen heteroatoms which bears one or two thioxo substituents, and which heterocyclic moiety may optionally bear one, two or three further substituents selected from halogeno, hydroxy, cyano, amino, (1–4C)alkyl, (1–4C)alkoxy, fluoro-(1–4C)alkyl, (1–4C)alkylamino, di-[(1–4C)alkyl]amino, amino-(1–4C)alkyl, (1–4C)alkylamino-(1–4C)alkyl, di-[(1–4C)alkyl]amino-(1–4C)alkyl, phenyl and phenyl-(1–4C)alkyl, and wherein said phenyl or phenyl-(1–4C)alkyl substituent may optionally bear a substituent selected from halogeno, (1–4C)alkyl and (1–4C)alkoxy;

wherein $A^1$ is a direct link to $X^1$ or is (1–3C)alkylene;
wherein $X^1$ is oxy, thio, sulphinyl, sulphonyl or imino;
wherein Ar is phenylene which may optionally bear one or two substituents selected from halogeno, hydroxy, amino, nitro, cyano, carbamoyl, ureido, (1–4C)alkyl, (1–4C)alkoxy, (1–4C)alkylamino, di-[(1–4C)alkyl]amino, fluoro-(1–4C)alkyl and (2–4C)alkanoylamino; or
Ar is pyridylene;
wherein $R^1$ is (1–4C)alkyl, (3–4C)alkenyl or (3–4C)alkynyl; and
wherein $R^2$ and $R^3$ together form a group of the formula —$A^2$—$X^2$—$A^3$— which, together with the carbon atom to which $A^2$ and $A^3$ are attached, defines a ring having 5 to 7 ring atoms, wherein $A^2$ and $A^3$, which may be the same or different, each is (1–3C)alkylene and $X^2$ is oxy, thio, sulphinyl or sulphonyl, and which ring may bear one, two or three substituents, which may be the same or different, selected from hydroxy, (1–4C)alkyl and (1–4C)alkoxy;
or wherein $R^1$ and $R^2$ together form a group of the formula —$A^2$—$X^2$—$A^3$— which, together with the oxygen atom to which $A^2$ is attached and with the carbon atom to which $A^3$ is attached, defines a ring having 5 to 7 ring atoms, wherein $A^2$ and $A^3$, which may be the same or different, each is (1–3C)alkylene and $X^2$ is oxy, thio, sulphinyl or sulphonyl, and which ring may bear one, two or three (1–4C)alkyl substituents, and wherein $R^3$ is (1–4C)alkyl, (2–4C)alkenyl or (2–4C)alkynyl; or a pharmaceutically-acceptable salt thereof.

The chemical formulae referred to herein by Roman numerals are set out for convenience on a separate sheet hereinafter.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of the formula I defined above may exhibit the phenomenon of tautomerism and any formula drawing presented herein may represent only one of the possible tautomeric forms, the invention includes in its definition any tautomeric form of a compound of the formula I which possesses the property of inhibiting 5-LO and is not to be limited merely to any one tautomeric form utilised within the formulae drawings.

It is further to be understood that, insofar as certain of the compounds of formula I defined above may exist in optically active or racemic forms by virtue of one or more substituents containing an asymmetric carbon atom, the invention includes in its definition any such optically active or racemic form which possesses the property of inhibiting 5-LO. The synthesis of optically active forms may be carried out by standard techniques of organic chemistry well known in the art, for example by synthesis from optically active starting materials or by resolution of a racemic form. Similarly, inhibitory properties against 5-LO may be evaluated using the standard laboratory techniques referred to hereinafter.

Suitable values for the generic terms referred to above include those set out below.

A suitable value for Q when it is a 10-membered bicyclic heterocyclic moiety containing one or two nitrogen heteroatoms which bears one or two thioxo substituents is for example, a benzo-fused heterocyclic moiety such as 2-thioxo-1,2-dihydroquinolinyl, 2-thioxo-1,2,3,4-tetrahydroquinolinyl, 1-thioxo-1,2-dihydroisoquinolinyl, 1-thioxo-1,2,3,4-tetrahydroisoquinolinyl, 4-thioxo-3,4-dihydroquinazolinyl, 2-thioxo-1,2-dihydroquinazolinyl, 2-thioxo-1,2-dihydroquinoxalinyl, 2-thioxo-1,2,3,4-tetrahydroquinoxalinyl, 2,3-dithioxo-1,2,3,4-tetrahydroquinoxalinyl or 2,4-dithioxo-1,2,3,4-tetrahydroquinazolinyl, or, for example, a pyrido-fused heterocyclic moiety such as 2-thioxo-1,2-dihydro-1,7-naphthyridinyl, 2-thioxo-1,2,3,4-tetrahydro-1,7-naphthyridinyl, 2-thioxo-1,2-dihydro-1,8-naphthyridinyl or 2-thioxo-1,2,3,4-tetrahydro-1,8-naphthyridinyl. The heterocyclic moiety may be attached through any available position including from either of the two rings of the bicyclic heterocyclic moiety and including through an available nitrogen atom. The heterocyclic moiety may bear a suitable substituent on an available nitrogen atom such as, for example, a (1–4C)alkyl, di-[(1–4C)alkyl]amino-(1–4C)alkyl, phenyl or phenyl-(1–4C)alkyl substituent on any such available nitrogen atom.

Suitable values for substituents which may be present on Q or Ar, or on a phenyl or phenyl-(1–4C)alkyl substituent on Q, include, for example:

| for halogeno: | fluoro, chloro, bromo and iodo; |
|---|---|
| for (1–4C)alkyl: | methyl, ethyl, propyl, isopropyl, butyl, isobutyl and sec-butyl; |
| for (1–4C)alkoxy: | methoxy, ethoxy, propoxy, isopropoxy and butoxy; |
| for fluoro-(1–4C)alkyl: | fluoromethyl, difluoromethyl, trifluoromethyl, 2-fluoroethyl, 2,2,2-trifluoroethyl and pentafluoroethyl; |
| for (1–4C)alkylamino: | methylamino, ethylamino, propylamino and butylamino; and |
| for di-[(1–4C)alkyl]amino: | dimethylamino, diethylamino and dipropylamino. |

Suitable values for substituents which may be present on Q include, for example:

| for amino-(1–4C)alkyl: | aminomethyl, 1-aminoethyl, 2-aminoethyl, 2-aminopropyl and 3-aminopropyl; |
|---|---|
| for (1–4C)alkylamino-(1–4C)-alkyl: | methylaminomethyl, 2-methylaminoethyl, 3-methylaminopropyl, ethylaminomethyl and 2-ethylaminoethyl; |
| for di-[(1–4C)alkyl]amino-(1–4C)alkyl: | dimethylaminomethyl, 2-dimethylaminoethyl, 3-dimethylaminopropyl, diethylaminomethyl and 2-diethylaminoethyl; |
| for phenyl-(1–4C)alkyl: | benzyl, phenethyl and 3-phenylpropyl. |

A suitable value for $A^1$ when it is (1–3C)alkylene is, for example, methylene, ethylene or trimethylene.

A suitable value for Ar when it is phenylene is, for example, 1,3-phenylene or 1,4-phenylene.

A suitable value for Ar when it is pyridylene is, for example, 3,5- or 2,6-pyridylene.

A suitable value for a (2–4C)alkanoylamino substituent which may be present on Ar is, for example, acetamido, propionamido or butyramido.

A suitable value for $R^1$ when it is (1–4C)alkyl is, for example, methyl, ethyl, propyl or butyl; when it is (3–4C)alkenyl is, for example, allyl, 2-butenyl or 3-butenyl; and when it is (3–4C)alkynyl is, for example, 2-propynyl or 2-butynyl.

When $R^2$ and $R^3$ together form a group of the formula —$A^2$—$X^2$—$A^3$— which, together with the carbon atom to which $A^2$ and $A^3$ are attached, defines a ring having 5 to 7 ring atoms then a suitable value for $A^2$ or $A^3$, which may be the same or different, when each is (1–3C)alkylene is, for example, methylene, ethylene or trimethylene. Suitable values for the substituents which may be present on said 5- to 7-membered ring include for example:

| for (1–4C)alkyl: | methyl, ethyl, propyl, isopropyl, butyl and isobutyl; |
|---|---|
| for (1–4C)alkoxy: | methoxy, ethoxy, propoxy, isopropoxy and butoxy. |

When $R^1$ and $R^2$ together form a group of the formula —$A^2$—$X^2$—$A^3$— which together with the oxygen atom to which $A^2$ is attached and with the carbon atom to which $A^3$ is attached, defines a ring having 5 to 7 ring atoms then a suitable value for $A^2$ or $A^3$, which may be the same or different, when each is (1–3C)alkylene is, for example, methylene, ethylene or trimethylene. Suitable values for the (1–4C)alkyl substituents which may be present on said 5- to 7-membered ring include, for example, methyl, ethyl, propyl, isopropyl and butyl.

A suitable value for $R^3$ when it is (1–4C)alkyl is, for example, methyl, ethyl, propyl or butyl; when it is (2–4C)alkenyl is, for example, vinyl, allyl, 2-butenyl or 3-butenyl; and when it is (2–4C)alkynyl is, for example, ethynyl, 2-propynyl or 2-butynyl.

A suitable pharmaceutically-acceptable salt of a thioxo heterocycle of the invention is, for example, an acid-addition salt of a thioxo heterocycle of the invention which is sufficiently basic, for example, an acid-addition salt with, for example, an inorganic or organic acid, for example hydrochloric, hydrobromic, sulphuric, phosphoric, trifluoroacetic, citric or maleic acid. In addition a suitable pharmaceutically-acceptable salt of a thioxo heterocycle of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Particular novel compounds of the invention are, for example, thioxo heterocycles of the formula I wherein:
(a) Q is a 10-membered benzo-fused heterocyclic moiety containing one or two nitrogen heteroatoms which bears one thioxo substituent, and which heterocyclic moiety may optionally bear one, two or three further substituents having the meanings defined hereinbefore for further substituents on Q; and $A^1$, $X^1$, Ar, $R^1$, $R^2$ and $R^3$ have any of the meanings defined hereinbefore;
(b) Q is 2-thioxo-1,2-dihydroquinolinyl or 2-thioxo-1,2,3,4-tetrahydroquinolinyl which may optionally bear one, two or three substituents having the meanings defined hereinbefore for further substituents on Q; and $A^1$, $X^1$, Ar, $R^1$, $R^2$ and $R^3$ have any of the meanings defined hereinbefore;
(c) Q is 2-thioxo-1,2-dihydroquinolin-5-yl, 2-thioxo-1,2-dihydroquinolin-6-yl, 2-thioxo-1,2-dihydroquinolin-7-yl, 2-thioxo-1,2,3,4-tetrahydroquinolin-5-yl, 2-thioxo-1,2,3,4-tetrahydroquinolin-6-yl or 2-thioxo-1,2,3,4-tetrahydroquinolin-7-yl which may optionally bear one, two or three substituents having the meanings defined hereinbefore for further substituents on Q; and $A^1$, $X^1$, Ar, $R^1$, $R^2$ and $R^3$ have any of the meanings defined hereinbefore;

(d) $A^1$ is a direct link to $X^1$, and $X^1$ is oxy, thio, sulphinyl or sulphonyl; and Q, Ar, $R^1$, $R^2$ and $R^3$ have any of the meanings defined hereinbefore;

(e) $A^1$ is methylene and $X^1$ is oxy, thio, sulphinyl or sulphonyl; and Q, Ar, $R^1$, $R^2$ and $R^3$ have any of the meanings defined hereinbefore;

(f) Ar is 1,3-phenylene or 1,4-phenylene which may optionally bear one or two substituents selected from fluoro, chloro, hydroxy, amino, nitro, ureido, methyl, methoxy, methylamino, dimethylamino, trifluoromethyl and acetamido; and Q, $A^1$, $X^1$, $R^1$, $R^2$ and $R^3$ have any of the meanings defined hereinbefore;

(g) Ar is 3,5-pyridylene; and Q, $A^1$, $X^1$, $R^1$, $R^2$ and $R^3$ have any of the meanings defined hereinbefore;

(h) $R^1$ is methyl, ethyl, allyl or 2-propynyl; and Q, $A^1$, $X^1$, Ar, $R^2$ and $R^3$ have any of the meanings defined hereinbefore;

(i) $R^2$ and $R^3$ together form a group of the formula —$A^2$—$X^2$—$A^3$— which, together with the carbon atom to which $A^2$ and $A^3$ are attached, defines a ring having 5 to 7 ring atoms, wherein $A^2$ and $A^3$, which may be the same or different, each is methylene, ethylene or trimethylene and $X^2$ is oxy, and which ring may bear one or two substituents selected from hydroxy, methyl, ethyl, propyl, methoxy and ethoxy; and Q, $A^1$, $X^1$, Ar and $R^1$ have any of the meanings defined hereinbefore; or (j) $R^1$ and $R^2$ together form a group of the formula —$A^2$—$X^2$—$A^3$— which, together with the oxygen atom to which $A^2$ is attached and with the carbon atom to which $A^3$ is attached, defines a ring having 5 to 7 ring atoms, wherein $A^2$ and $A^3$, which may be the same or different, each is methylene or ethylene and $X^2$ is oxy, and which ring may bear one, two or three substituents selected from methyl, ethyl and propyl, and $R^3$ is methyl or ethyl; and Q, $A^1$, $X^1$ and Ar have any of the meanings defined hereinbefore;

or a pharmaceutically-acceptable salt thereof.

A preferred compound of the invention comprises a thioxo heterocycle of the formula I
wherein Q is 2-thioxo-1,2-dihydroquinolinyl or 2-thioxo-1,2,3,4-tetrahydroquinolinyl which may optionally bear one, two or three substituents selected from fluoro, chloro, bromo, hydroxy, cyano, amino, methyl, ethyl, propyl, methoxy, trifluoromethyl, 2-fluoroethyl, 2,2,2-trifluoroethyl, 2-methylaminoethyl, 2-dimethylaminoethyl, phenyl and benzyl, and wherein said phenyl or benzyl substituent may optionally bear a substituent selected from chloro, methyl and methoxy;

$A^1$ is a direct link to $X^1$ or is methylene;

$X^1$ is oxy, thio, sulphinyl or sulphonyl;

Ar is 1,3-phenylene or 1,4-phenylene which may optionally bear one or two substituents selected from fluoro, chloro, hydroxy, amino, nitro, ureido, methoxy, dimethylamino, trifluoromethyl and acetamido; or Ar is 3,5-pyridylene;

$R^1$ is methyl, ethyl, allyl or 2-propynyl; and $R^2$ and $R^3$ together form a group of the formula —$A^2$—$X^2$—$A^3$— which, together with the carbon atom to which $A^2$ and $A^3$ are attached, defines a ring having 5 or 6 ring atoms, wherein $A^2$ is ethylene, $A^3$ is methylene or ethylene, and $X^2$ is oxy, and which ring may bear one or two substituents selected from methyl, ethyl, propyl, methoxy and ethoxy;

or $R^1$ and $R^2$ together form a group of the formula —$A^2$—$X^2$—$A^3$— which, together with the oxygen atom to which $A^2$ is attached and with the carbon atom to which $A^3$ is attached, defines a ring having 5 or 6 ring atoms, wherein $A^2$ is methylene, $A^3$ is methylene or ethylene, and $X^2$ is oxy, and which ring may bear one, two or three substituents selected from methyl, ethyl and propyl, and $R^3$ is methyl or ethyl;

or a pharmaceutically-acceptable salt thereof.

A further preferred compound of the invention comprises a thioxo heterocycle of the formula I wherein Q is 2-thioxo-1,2-dihydroquinolin-6-yl or 2-thioxo-1,2,3,4-tetrahydroquinolin-6-yl which may optionally bear one or two substituents selected from fluoro, chloro, methyl, ethyl, propyl, 2-fluoroethyl, 2-dimethylaminoethyl, phenyl and benzyl;

$A^1$ is a direct link to $X^1$, or is methylene;

$X^1$ is oxy, thio, sulphinyl or sulphonyl;

Ar is 1,3-phenylene or 1,4-phenylene which may optionally bear one or two substituents selected from fluoro, hydroxy, amino, nitro, ureido, methoxy, dimethylamino, trifluoromethyl and acetamido; or Ar is 3,5-pyridylene;

$R^1$ is methyl, ethyl, allyl or 2-propynyl; and $R^2$ and $R^3$ together form a group of the formula —$A^2$—$X^2$—$A^3$— which, together with the carbon atom to which $A^2$ and $A^3$ are attached, defines a ring having 5 or 6 ring atoms, wherein $A^2$ is ethylene, $A^3$ is methylene or ethylene, and $X^2$ is oxy, and which ring may bear one or two substituents selected from methyl and ethyl;

or $R^1$ and $R^2$ together form a group of the formula —$A^2$—$X^2$—$A^3$— which, together with the oxygen atom to which $A^2$ is attached and with the carbon atom to which $A^3$ is attached, defines a ring having 5 ring atoms, wherein $A^2$ is methylene, $A^3$ is methylene, and $X^2$ is oxy, and which ring may bear one, two or three substituents selected from methyl and ethyl and $R^3$ is methyl or ethyl;

or a pharmaceutically-acceptable salt thereof.

A further preferred compound of the invention comprises a thioxo heterocycle of the formula I wherein Q is 2-thioxo-1,2-dihydroquinolin-6-yl or 2-thioxo-1,2,3,4-tetrahydroquinolin-6-yl which may optionally bear one substituent selected from methyl and ethyl;

$A^1$ is a direct link to $X^1$, or is methylene;

$X^1$ is oxy, thio, sulphinyl or sulphonyl;

Ar is 1,3-phenylene which may optionally bear one or two substituents selected from fluoro, methoxy and trifluoromethyl;

$R^1$ is methyl, ethyl or allyl; and $R^2$ and $R^3$ together form a group of the formula —$A^2$—$X^2$—$A^3$— which, together with the carbon atom to which $A^2$ and $A^3$ are attached, defines a ring having 5 or 6 ring atoms, wherein $A^2$ ethylene, $A^3$ is methylene or ethylene and $X^2$ is oxy, and which ring may bear a substituent selected from methyl, ethyl, propyl and methoxy;

or a pharmaceutically-acceptable salt thereof.

A further preferred compound of the invention comprises a thioxo heterocycle of the formula I wherein Q is 1-methyl-2-thioxo-1,2-dihydroquinolin-6-yl or 1-methyl-2-thioxo-1,2,3,4-tetrahydroquinolin-6-yl;

$A^1$ is methylene; $X^1$ is oxy;

Ar is 1,3-phenylene or 5-fluoro-1,3-phenylene;

$R^1$ is methyl; and $R^2$ and $R^3$ together form a group of the formula $-A^2-X^2-A^3-$ which, together with the carbon atom to which $A^2$ and $A^3$ are attached, defines a ring having 6 ring atoms, wherein each of $A^2$ and $A^3$ is ethylene and $X^2$ is oxy, and which ring may bear a methyl or ethyl substituent alpha to $X^2$;

or a pharmaceutically-acceptable salt thereof.

A further preferred compound of the invention comprises a thioxo heterocycle of the formula I wherein Q is 1-methyl-2-thioxo-1,2-dihydroquinolin-6-yl or 1-methyl-2-thioxo-1,2,3,4-tetrahydroquinolin-6-yl;

$A^1$ is methylene and $X^1$ is oxy, or $A^1$ is a direct link to $X^1$ and $X^1$ is thio;

Ar is 1,3-phenylene or 5-fluoro-1,3-phenylene;

$R^1$ is methyl; and $R^2$ and $R^3$ together form a group of the formula $-A^2-X^2-A^3-$ which, together with the carbon atom to which $A^2$ and $A^3$ are attached, defines a ring having 6 ring atoms, wherein each of $A^2$ and $A^3$ is ethylene and $X^2$ is oxy, and which ring may bear a methyl or ethyl substituent alpha to $X^2$;

or a pharmaceutically-acceptable salt thereof.

Specific especially preferred compounds of the invention include, for example, the following thioxo heterocycles of the formula I, or pharmaceutically-acceptable salts thereof:

4-[5-fluoro-3-(1-methyl-2-thioxo-1,2-dihydroquinolin-6-ylmethoxy)phenyl]-4-methoxytetrahydropyran and 4-[5-fluoro-3-(1-methyl-2-thioxo-1,2,3,4-tetrahydroquinolin-6-ylmethoxy)phenyl]-4-methoxytetrahydropyran.

A further especially preferred compound of the invention is the thioxo heterocycle of the formula I, or a pharmaceutically-acceptable salt thereof:

4-[5-fluoro-3-(1-methyl-2-thioxo-1,2,3,4-tetrahydroquinolin-6-ylthio)phenyl]-4-methoxytetrahydropyran.

A compound of the invention comprising a thioxo heterocycle of the formula I, or a pharmaceutically-acceptable salt thereof, may be prepared by any process known to be applicable to the preparation of structurally-related compounds. Such procedures are provided as a further feature of the invention and are illustrated by the following representative examples in which, unless otherwise stated, Q, $A^1$, $X^1$, Ar, $R^1$, $R^2$ and $R^3$ have any of the meanings defined hereinbefore.

(a) The coupling, preferably in the presence of a suitable base, of a compound of the formula $Q-A^1-X^1-H$ with a compound of the formula II wherein Z is a displaceable group; provided that, when there is an amino, alkylamino or hydroxy group in Q, Ar, $R^2$ or $R^3$, any amino, alkylamino or hydroxy group may be protected by a conventional protecting group or alternatively any such group need not be protected, whereafter any undesired protecting group in Q, Ar, $R^2$ or $R^3$ is removed by conventional means.

A suitable displaceable group Z is, for example, a halogeno or sulphonyloxy group, for example a fluoro, chloro, bromo, iodo, methanesulphonyloxy or toluene-p-sulphonyloxy group.

A suitable base for the coupling reaction is, for example, an alkali or alkaline earth metal carbonate, (1–4C-)alkoxide, hydroxide or hydride, for example sodium carbonate, potassium carbonate, sodium ethoxide, sodium butoxide, sodium hydroxide, potassium hydroxide, sodium hydride or potassium hydride; or an organometallic base such as (1–4C)alkyl-lithium, for example n-butyl-lithium. The coupling reaction is conveniently performed in a suitable inert solvent or diluent, for example N,N-dimethylformamide, N,N-dimethylacetamide, N-methylpyrrolidin-2-one, dimethylsulphoxide, acetone, 1,2-dimethoxyethane or tetrahydrofuran, and at a temperature in the range, for example, 10° to 150° C., conveniently at or near 100° C.

Conveniently the reaction may be performed in the presence of a suitable catalyst, for example a metallic catalyst, for example palladium(O) or copper(I) such as tetrakis(triphenylphosphine)palladium, cuprous chloride or cuprous bromide.

A suitable protecting group for an amino or alkylamino group is, for example, an acyl group for example a (2–4C)alkanoyl group (especially acetyl), a (1–4C)alkoxycarbonyl group (especially methoxycarbonyl, ethoxycarbonyl or tert-butoxycarbonyl), an arylmethoxycarbonyl group (especially benzyloxycarbonyl) or an aroyl group (especially benzoyl). The deprotection conditions for the above protecting groups necessarily vary with the choice of protecting group. Thus, for example, an acyl group such as an alkanoyl or alkoxycarbonyl or an aroyl group may be removed for-example, by hydrolysis with a suitable base such as an alkali metal hydroxide, for example lithium or sodium hydroxide. Alternatively an acyl group such as a tert-butoxycarbonyl group may be removed, for example, by treatment with a suitable acid such as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-charcoal.

A suitable protecting group for a hydroxy group is, for example, an acyl group, for example a (2–4C)alkanoyl group (especially acetyl), an aroyl group (especially benzoyl) or an arylmethyl group (especially benzyl). The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-charcoal.

The starting materials of the formula $Q-A^1-X^1-H$ and of the formula II may be obtained by standard procedures of organic chemistry. Thus, for example, when a starting material of the formula Q-SH is required, it may be obtained by, for example, the reaction of a heterocyclic moiety of the formula Q-H as defined hereinbefore with a halosulphonylating agent such as, for example, chlorosulphonic acid, in a suitable solvent or diluent, for example dichloroethane or pyridine, and at a temperature in the range, for example 40° to 150° C., conveniently at or near 100° C. The intermediate of, for example, the formula $Q-SO_2-Cl$ so produced may be reduced to a compound of the formula Q—SH by a conventional reducing agent such as, for example, a suitable reducing metallic salt such as a metallic halide, for example a stannous halide, conveniently stannous chloride, in a suitable solvent or diluent such as a (2–4C)alkanoic acid, for example acetic acid, and at a temperature in the range, for example, 40° to 150° C., conveniently in the range 80° to 100° C. Alternatively the reducing agent may be a suitable reducing metal, such as zinc or iron, in the presence of a strong acid, such as hydrochloric, sulphuric or phosphoric acid, and at a temperature in the range, for example 10° to 150° C., conveniently at or near 100° C. Alternatively the reducing agent may be a tri-(1–4C)alkylsilyl halide, conveniently trimethylsilyl iodide, in a suitable solvent or diluent such as methylene chloride and at a temperature at or near ambient temperature.

Conveniently intermediates of the formula II wherein Z, Ar, $R^1$, $R^2$ and $R^3$ have the meanings defined hereinbefore, may be obtained by way of compounds of the formula Z-Ar-Y, wherein Z and Ar have the meanings defined hereinbefore and Y is, for example, a halogeno, formyl, alkanoyl, nitrile or alkoxycarbonyl group, as illustrated in accompanying Scheme I (set out hereinafter).

It will also be appreciated that the intermediate of the formula II may conveniently be obtained from the compound of the formula Z-Ar-Y, as defined hereinbefore, by reversing the order of introduction of the groups $R^2$ and $R^3$ which is used in Scheme I.

(b) The coupling, preferably in the presence of a suitable base as defined hereinbefore, of a compound of the formula III with a compound of the formula Q-$A^1$-Z wherein Z is a displaceable group as defined hereinbefore; provided that, when there is an amino, alkylamino or hydroxy group in Q, Ar, $R^2$ or $R^3$, any amino, alkylamino or hydroxy group may be protected by a conventional protecting group as defined hereinbefore or alternatively any such group need not be protected, whereafter any undesired protecting group in Q, Ar, $R^2$ or $R^3$ is removed by conventional means.

The coupling reaction is conveniently performed in a suitable inert solvent as defined hereinbefore and at a temperature in the range, for example, 10° to 150° C., conveniently at or near 100° C. The reaction may conveniently be performed in the presence of a suitable catalyst as defined hereinbefore.

The starting materials of the formula Q—$A^1$—Z and of the formula III may be obtained by standard procedures of organic chemistry. The preparation of starting materials of the formula III is described within the accompanying non-limiting Examples which are provided for the purpose of illustration only. Alternatively necessary starting materials are obtainable by analogous procedures to those illustrated in accompanying Scheme II (set out hereinafter) or by modifications thereto which are within the ordinary skill of an organic chemist.

A suitable protecting group $R^4$, as employed in Scheme II, is any one of the many such groups known in the art and includes any appropriate protecting group as defined hereinbefore. Examples of such groups are given in Scheme II. The conditions for the introduction and removal of such protecting groups are described in standard textbooks of organic chemistry such as, for example, "Protective Groups in Organic Synthesis" by T. W. Green (J. Wiley and Sons, 1981).

(c) The alkylation, preferably in the presence of a suitable base as defined hereinbefore, of a compound of the formula IV with a compound of the formula $R^1$—Z, wherein $R^1$ and Z have the meanings defined hereinbefore; provided that, when there is an amino, imino, alkylamino or hydroxy group in Q, $X^1$, Ar, $R^2$ or $R^3$ any amino, imino, alkylamino or hydroxy group may be protected by a conventional protecting group or alternatively any such group need not be protected, whereafter any undesired protecting group in Q, $X^1$, Ar, $R^2$ or $R^3$ is removed by conventional means.

A suitable protecting group for an imino group is, for example, any of the protecting groups defined hereinbefore for an amino or alkylamino group.

The tertiary alcohol starting material of the formula IV may be obtained by standard procedures of organic chemistry. Conveniently, and as illustrated in accompanying Scheme III (set out hereinafter), intermediates of the formulae Q-$A^1$-$X^1$-Ar-Y, wherein Q, $A^1$, $X^1$ and Ar have the meanings defined hereinbefore and Y is, for example, a halogeno, formyl, alkanoyl, nitrile or alkoxycarbonyl group may be utilised in the preparation of the tertiary alcohol starting material of the formula IV.

(d) For the production of those compounds of the formula I wherein $R^1$ and $R^2$ together form a group of the formula —$A^2$—$X^2$—$A^3$— which, together with the oxygen atom to which $A^2$ is attached, defines a ring having 5 to 7 ring atoms and wherein $A^2$, $X^2$ and $A^3$ have the meanings defined hereinbefore, and wherein $R^3$ has the meaning defined hereinbefore; the cyclisation of a compound of the formula V upon reaction with an appropriate aldehyde or ketone, or with a hemiacetal or acetal thereof, or with a compound of the formula Z—$A^2$—Z, wherein Z has the meaning defined hereinbefore; provided that, when there is an amino, imino, alkylamino or hydroxy group in Q, $X^1$ or Ar, any amino, imino, alkylamino or hydroxy group is protected by a conventional protecting group, whereafter any undesired protecting group in Q, $X^1$ or Ar is removed by conventional means.

The cyclisation of a compound of the formula V with an appropriate aldehyde or ketone, or with a hemiacetal or acetal thereof, is conveniently carried out in the presence of a suitable acid. A suitable acid for the cyclisation reaction is, for example, an inorganic acid such as hydrochloric, sulphuric or phosphoric acid, or, for example, an organic acid such as p-toluenesulphonic acid or trifluoroacetic acid. The cyclisation reaction is conveniently performed in a suitable inert solvent or diluent, for example 1,2-dimethoxyethane or tetrahydrofuran. Preferably the reaction is performed using the appropriate aldehyde or ketone, or a hemiacetal or acetal derivative thereof, as both a reactant and diluent. The cyclisation is effected at a temperature in the range, for example, 20° to 150° C., conveniently at or near the boiling point of the diluent or solvent.

The cyclisation of a compound of the formula V with a compound of the formula Z—$A^2$—Z is conveniently carried out in the presence of a suitable base as defined hereinbefore.

The tertiary alcohol starting material of the formula V may be obtained by standard procedures of organic chemistry. Conveniently, and as illustrated in accompanying Scheme IV (set out hereinafter), intermediates of the formula Q—$A^1$—$X^1$—Ar—Y, wherein Q, $A^1$, $X^1$, Ar and Y have the meanings defined hereinbefore, may be utilised in the preparation of the tertiary alcohol starting material of the formula V.

A suitable protecting group $R^4$, as defined hereinbefore, is employed.

(e) The reaction of a heterocycle of the formula I wherein Q is a 10-membered bicyclic heterocyclic moiety containing one or two nitrogen heteroatoms which bears one or two oxo substituents with a thiation reagent such that each oxo substituent is converted into a thioxo substituent; provided that, when there is an amino, imino, alkylamino or hydroxy group in Q, $X^1$, Ar, $R^2$ or $R^3$ any such group may be protected by a conventional protecting group or alternatively any such group need not be protected, whereafter an undesired protecting group in Q, $X^1$, Ar, $R^2$ and $R^3$ is removed by conventional means.

A suitable thiation reagent is, for example, any agent known in the art for the conversion of an oxo group to a thioxo group such as, for example, 2,4-bis-(4-methoxyphenyl)-1,3-dithia-2,4-diphosphetane-2,4-disulphide (Lawesson's Reagent) or phosphorus pentasulphide. The thiation reaction is generally carried out with the required stoichiometric amount of thiation reagent in order to reduce the risk of damage to other functional groups. In general the reaction is carried out in a suitable solvent or diluent such as toluene, xylene or tetrahydrofuran and at a temperature, for example, at or near the reflux temperature of the solvent or diluent, that is in the range 65° to 150° C.

(f) For the production of those compounds of the formula I wherein $X^1$ is a sulphinyl or sulphonyl group, wherein $R^2$ and $R^3$ together form a group of the formula $—A^2—X^2—A^3—$ and $X^2$ is a sulphinyl or sulphonyl group or wherein $R^1$ and $R^2$ together form a group of the formula $—A^2—X^2—A^3—$ and $X^2$ is a sulphinyl or sulphonyl group, the oxidation of a compound of the formula I wherein $X^1$ is a thio group, wherein $R^2$ and $R^3$ together form a group of the formula $—A^2—X^2—A^3—$ and $X^2$ is a thio group or wherein $R^1$ and $R^2$ together form a group of the formula $—A^2—X^2—A^3—$ and $X^2$ is a thio group.

A suitable oxidising agent is, for example, any agent known in the art for the oxidation of thio to sulphinyl and/or sulphonyl, for example, hydrogen peroxide, a peracid (such as 3-chloroperoxybenzoic or peroxyacetic acid), an alkali metal peroxysulphate (such as potassium peroxymonosulphate), chromium trioxide or gaseous oxygen in the presence of platinum. The oxidation is generally carried out under as mild conditions as possible and with the required stoichiometric amount of oxidising agent in order to reduce the risk of over oxidation and damage to other functional groups. In general the reaction is carried out in a suitable solvent or diluent such as methylene chloride, chloroform, acetone, tetrahydrofuran or tert-butyl methyl ether and at a temperature, for example, at or near ambient temperature, that is in the range 15° to 35° C. When a compound carrying a sulphinyl group is required a milder oxidising agent may also be used, for example sodium or potassium metaperiodate, conveniently in a polar solvent such as acetic acid or ethanol. It will be appreciated that when a compound of the formula I containing a sulphonyl group is required, it may be obtained by oxidation of the corresponding sulphinyl compound as well as of the corresponding thio compound.

(g) For the production of those compounds of the formula I wherein Ar bears an alkanoylamino substituent, the acylation of a compound of the formula I wherein Ar bears an amino substituent.

A suitable acylating agent is, for example, any agent known in the art for the acylation of amino to acylamino, for example an acyl halide, for example a (2-6C)alkanoyl chloride or bromide, in the presence of a suitable base, an alkanoic acid anhydride, for example a (2-6C)alkanoic acid anhydride, or an alkanoic acid mixed anhydride, for example the mixed anhydride formed by the reaction of an alkanoic acid and a (1-4C)alkoxycarbonyl halide, for example a (1-4C)alkoxycarbonyl chloride, in the presence of a suitable base. In general the reaction is carried out in a suitable solvent or diluent such as methylene chloride, acetone, tetrahydrofuran or tert-butyl methyl ether and at a temperature, for example, at or near ambient temperature, that is in the range 15° to 35° C. A suitable base when it is required is, for example, pyridine, 4-dimethylaminopyridine, triethylamine, ethyldiisopropylamine, N-methylmorpholine, an alkali metal carbonate, for example potassium carbonate, or an alkali metal carboxylate, for example sodium acetate.

(h) For the production of those compounds of the formula I wherein Q bears an alkyl or substituted alkyl substituent on an available nitrogen atom, or wherein Ar bears an alkoxy or substituted alkoxy substituent, the alkylation of a compound of the formula I wherein Q bears a hydrogen atom on said available nitrogen atom, or wherein Ar bears a hydroxy substituent.

A suitable alkylating agent is, for example, any agent known in the art for the alkylation of an available nitrogen atom, or of a hydroxy group, for example an alkyl or substituted alkyl halide, for example a (1-6C)alkyl chloride, bromide or iodide or a substituted (1-4C)alkyl chloride, bromide or iodide, in the presence of a suitable base. A suitable base for the alkylation reaction is, for example, an alkali or alkaline earth metal carbonate, sodium hydroxide, potassium hydroxide, sodium hydride or potassium hydride. The alkylation reaction is preferably performed in a suitable inert solvent or diluent, for example N,N-dimethylformamide, dimethylsulphoxide, acetone, 1,2-dimethoxyethane or tetrahydrofuran, and at a temperature in the range, for example, 10° to 150° C., conveniently at or near ambient temperature.

When a pharmaceutically-acceptable salt of a novel compound of the formula I is required, it may be obtained, for example, by reaction of said compound with a suitable acid or base using a conventional procedure. When an optically active form of a compound of the formula I is required, it may be obtained by carrying out one of the aforesaid procedures using an optically active starting material, or by resolution of a racemic form of said compound using a conventional procedure.

Many of the intermediates defined herein are novel, for example those of the formulae IV and V and these are provided as a further feature of the invention.

As stated previously, the novel compounds of the formula I are inhibitors of the enzyme 5-LO. The effects of this inhibition may be demonstrated using one or more of the standard procedures set out below:

a) An in vitro spectrophotometric enzyme assay system, which assesses the inhibitory properties of a test compound in a cell free system using 5-LO isolated from guinea pig neutrophils and as described by D. Aharony and R. L. Stein (*J. Biol. Chem.*, 1986, 261(25), 11512-11519). This test provides a measure of the intrinsic inhibitory properties of a test compound against soluble 5-LO in an extracellular environment.

b) An in vitro assay system involving incubating a test compound with heparinised human blood, prior to challenge with the calcium ionophore A23187 and then indirectly measuring the inhibitory effects on 5-LO by assaying the amount of $LTB_4$ using specific radioimmunoassays described by Carey and Forder (F. Carey and R. A. Forder, *Prostaglandins Leukotrienes Med.*, 1986, 22, 57; *Prostaglandins,* 1984, 28, 666; *Brit. J. Pharmacol.* 1985, 84, 34P) which involve the use of a protein-$LTB_4$ conjugate produced using the procedure of Young et alia (*Prostaglandins,* 1983, 26(4), 605-613). The effects of a test compound on the enzyme cyclooxygenase (which is involved in the alternative metabolic pathway for arachidonic acid and gives rise to prostaglandins, thromboxanes and related metabolites) may be measured at the same time using the specific radioimmunoassay for thromboxane $B_2(TxB_2)$ described by Carey and Forder (see above). This test provides an indication of the effects of a test compound against 5-LO and also cyclooxygenase in the presence of blood cells and proteins. It permits the selectivity of the inhibitory effect on 5-LO or cyclooxygenase to be assessed.

c) An ex vivo assay system, which is a variation of test b) above, involving administration of a test compound (usually orally as the suspension produced when a solution of the test compound in dimethylsulphoxide is added to carboxymethylcellulose), blood collection, heparinisation, challenge with A23187 and radioimmunoassay of $LTB_4$ and $TxB_2$. This test provides an indication of the bioavailability of a test compound as an inhibitor of 5-LO or cyclooxygenase.

d) An in vitro assay system involving the measurement of the inhibitory properties of a test compound against the liberation of $LTC_4$ and $PGE_2$ induced by zymosan on mouse resident peritoneal macrophages, using the procedure of Humes (J. L. Humes et alia, *Biochem. Pharmacol.*, 1983, 32, 2319-2322) and conventional radioimmunoassay systems to measure $LTC_4$ and $PGE_2$. This test provides an indication of inhibitory effects against 5-LO and cyclooxygenase in a non-proteinaceous system.

e) An in vivo system involving the measurement of the effects of a test compound in inhibiting the inflammatory response to arachidonic acid in the rabbit skin model developed by D. Aked et alia (*Brit. J. Pharmacol.*, 1986, 89, 431-438). This test provides an in vivo model for 5-LO inhibitors administered topically or orally.

f) An in vivo system involving measuring the effects of a test compound administered orally or intravenously on a leukotriene dependent bronchoconstriction induced by an antigen challenge in guinea pigs pre-dosed with an antihistamine (mepyramine), a $\beta$-adrenergic blocking agent (propranolol) and a cyclooxygenase inhibitor (indomethacin), using the procedure of W. H. Anderson et alia (*British J. Pharmacology*, 1983, 78(1), 67-574). This test provides a further in vivo test for detecting 5-LO inhibitors.

g) An in vivo system involving measuring the effects of a test compound administered orally against the liberation of $LTB_4$ induced by zymosan within an air pouch generated within the subcutaneous tissue of the back of male rats. The rats are anaesthetised and air pouches are formed by the injection of sterile air (20 ml). A further injection of air (10 ml) is similarly given after 3 days. At 6 days after the initial air injection the test compound is administered (usually orally as the suspension produced when a solution of the test compound in dimethylsulphoxide is added to hydroxypropylmethylcellulose), followed by the intrapouch injection of zymosan (1 ml of a 1% suspension in physiological saline). After 3 hours the rats are killed, the air pouches are lavaged with physiological saline, and the specific radioimmunoassay described above is used to assay $LTB_4$ in the washings. This test provides an indication of inhibitory effects against 5-LO in an inflammatory milieu.

Although the pharmacological properties of the compounds of the formula I vary with structural changes as expected, in general compounds of the formula I possess 5-LO inhibitory effects at the following concentrations or doses in one or more of the above tests a)–f):

Test a): $IC_{50}$ in the range, for example, 0.01-30 $\mu M$;
Test b): $IC_{50}$ ($LTB_4$) in the range, for example, 0.01-40 $\mu M$
$IC_{50}$ ($TxB_2$) in the range, for example, 40-200 $\mu M$;
Test c): oral $ED_{50}(LTB_4)$ in the range, for example, 0.1-100 mg/kg;
Test d): $IC_{50}$ ($LTC_4$) in the range, for example, 0.001-1 $\mu M$,
$IC_{50}$ ($PGE_2$) in the range, for example, 20-1000 $\mu M$;
Test e): inhibition of inflammation in the range, for example, 0.3-100 $\mu g$ intradermally;
Test f): $ED_{50}$ in the range, for example, 0.5-10 mg/kg i.v.;
Test g): oral $ED_{50}(LTB_4)$ in the range, for example, 0.1-50 mg/kg.

No overt toxicity or other untoward effects are present in tests c), e), f) and/or g) when compounds of the formula I are administered at several multiples of their minimum inhibitory dose or concentration.

Thus, by way of example, the compound 4-[5-fluoro-3-(1-methyl-2-thioxo-1,2,3,4-tetrahydroquinolin-6-ylmethoxy)phenyl]-4-methoxytetrahydropyran has an $IC_{50}$ of 0.1 $\mu M$ against $LTB_4$ in test b), and an oral $ED_{50}$ of 1.5 mg/kg versus $LTB_4$ in test g); and the compound 4-[5-fluoro-3-(1-methyl-2-thioxo-1,2,3,4-tetrahydroquinolin-6-ylthio)phenyl]-4-methoxytetrahydropyran has an $IC_{50}$ of 0.05 $\mu M$ against $LTB_4$ in test b), and an oral $ED_{50}$ of 0.5 mg/kg versus $LTB_4$ in test g). In general those compounds of the formula I which are particularly preferred have an $IC_{50}$ of $<1$ $\mu M$ against $LTB_4$ in test b), and an oral $ED_{50}$ of $<100$ mg/kg against $LTB_4$ in tests c) and/or g).

These compounds are examples of compounds of the invention which show selective inhibitory properties for 5-LO as opposed to cyclooxygenase, which selective properties are expected to impart improved therapeutic properties, for example, a reduction in or freedom from the gastrointestinal side-effects frequently associated with cyclooxygenase inhibitors such as indomethacin.

According to a further feature of the invention there is provided a pharmaceutical composition which comprises a thioxo heterocycle of the formula I, or a pharmaceutically-acceptable salt thereof, in association with a pharmaceutically-acceptable diluent or carrier.

The composition may be in a form suitable for oral use, for example a tablet, capsule, aqueous or oily solution, suspension or emulsion; for topical use, for example a cream, ointment, gel or aqueous or oily solution or suspension; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general the above compositions may be prepared in a conventional manner using conventional excipients.

The amount of active ingredient (that is a thioxo heterocycle of the formula I, or a pharmaceutically-acceptable salt thereof) that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient.

According to a further feature of the invention there is provided a thioxo heterocycle of the formula I, or a pharmaceutically-acceptable salt thereof, for use in a method of treatment of the human or animal body by therapy.

The invention also includes a method of treating a disease or medical condition mediated alone or in part by one or more leukotrienes which comprises administering to a warm-blooded animal requiring such treatment an effective amount of an active ingredient as defined above. The invention also provides the use of such an active ingredient in the production of a new medicament for use in a leukotriene mediated disease or medical condition.

The size of the dose for therapeutic or prophylactic purposes of a compound of the formula I will naturally vary according to the nature and severity of the conditions, the age and sex of the animal or patient and the route of administration, according to well known principles of medicine. As mentioned above, compounds of the formula I are useful in treating those allergic and inflammatory conditions which are due alone or in part to the effects of the metabolites of arachidonic acid arising by the linear (5-LO catalysed) pathway and in particular the leukotrienes, the production of which is mediated by 5-LO. As previously mentioned, such conditions include, for example, asthmatic conditions, allergic reactions, allergic rhinitis, allergic shock, psoriasis, atopic dermatitis, cardiovascular and cerebrovascular disorders of an inflammatory nature, arthritic and inflammatory joint disease, and inflammatory bowel diseases.

In using a compound of the formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used.

Although the compounds of the formula I are primarily of value as therapeutic agents for use in warm-blooded animals (including man), they are also useful whenever it is required to inhibit the enzyme 5-LO. Thus, they are useful as pharmacological standards for use in the development of new biological tests and in the search for new pharmacological agents.

By virtue of their effects on leukotriene production, the compounds of the formula I have certain cytoprotective effects, for example they are useful in reducing or suppressing certain of the adverse gastrointestinal effects of the cyclooxygenase inhibitory non-steroidal anti-inflammatory agents (NSAIA), such as indomethacin, acetylsalicylic acid, iburprofen, sulindac, tolmetin and piroxicam. Furthermore, co-administration of a 5-LO inhibitor of the formula I with a NSAIA can result in a reduction in the quantity of the latter agent needed to produce a therapeutic effect, thereby reducing the likelihood of adverse side-effects. According to a further feature of the invention there is provided a pharmaceutical composition which comprises a thioxo heterocycle of the formula I, or a pharmaceutically-acceptable salt thereof as defined hereinbefore, in conjunction or admixture with a cyclooxygenase inhibitory non-steroidal anti-inflammatory agent (such as mentioned above), and a pharmaceutically-acceptable diluent or carrier.

The cytoprotective effects of the compounds of the formula I may be demonstrated, for example in a standard laboratory model which assesses protection against indomethacin-induced or ethanol-induced ulceration in the gastrointestinal tract of rats.

The compositions of the invention may in addition contain one or more therapeutic or prophylactic agents known to be of value for the disease under treatment. Thus, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a beta-adrenergic stimulant may usefully also be present in a pharmaceutical composition of the invention for use in treating a pulmonary disease or condition.

The invention will now be illustrated in the following non-limiting Examples in which, unless otherwise stated.

(i) evaporations were carried out by rotary evaporation in vacuo and work-up procedures were carried out after removal of residual solids by filtration;

(ii) operations were carried out at room temperature, that is in the range 18°–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Meck, Darmstadt, W. Germany;

(iv) yields are given for illustration only and are not necessarily the maximum attainable;

(v) the end-products of the formula I have satisfactory microanalyses and their structures were confirmed by NMR and mass spectral techniques;

(vi) intermediates were not generally fully characterised and purity was assessed by thin layer chromatographic, infra-red (IR) or NMR analysis;

(vii) melting points are uncorrected and were determined using a Mettler SP62 automatic melting point apparatus or an oil-bath apparatus; melting points for the end-products of the formula I were determined after crystallisation from a conventional organic solvent such as ethanol, methanol, acetone, ether or hexane, alone or in admixture; and (viii) the following abbreviations have been used:

| THF  | tetrahydrofuran;     |
|------|----------------------|
| DMSO | dimethylsulphoxide;  |
| DMF  | N,N-dimethylformamide; |
| DMA  | N,N-dimethylacetamide. |

EXAMPLE 1

2,4-Bis(4-methoxyphenyl)-1,3-dithia-2,4-diphosphetane-2,4-disulphide (Lawesson's Reagent, 0.4 g) was added portionwise to a solution of 4-[5-fluoro-3-(1-methyl-2-oxo-1,2-dihydroquinolin-6-ylmethoxy)-phenyl]-4-methoxytetrahydropyran (0.397 g) in toluene (10 ml) and the mixture was stirred and heated to reflux for 1.5 hours. The mixture was evaporated and the residue was purified by column chromatography using a 19:1 v/v mixture of methylene chloride and diethyl ether as eluent. There was thus obtained 4-[5-fluoro-3-(1-methyl-2-thioxo-1,2-dihydroquinolin-6-ylmethoxy)-phenyl]-4-methoxytetrahydropyran (0.068 g, 16%), m.p. 211°-213° C.

The 4-[5-fluoro-3-(1-methyl-2-oxo-1,2-dihydroquinolin-6-ylmethoxy)phenyl]-4-methoxytetrahydropyran used as a starting material was obtained as follows:

A mixture of 6-bromomethyl-1-methyl-1,2-dihydroquinolin-2-one (22.0 g), 4-(5-fluoro-3-hydroxyphenyl)-4-methoxytetrahydropyran (20.1 g), potassium carbonate (18.0 g) and DMF (300 ml) was stirred at ambient temperature for 16 hours. The mixture was evaporated and the residue was partitioned between ethyl acetate and water. The organic phase was washed with water and with brine, dried (MgSO$_4$) and evaporated to leave a white solid (35 g). The solid was purified by column chromatography using a 2:1 v/v mixture of methylene chloride and ethyl acetate as eluent. There was thus obtained the required starting material (30.3 g, 88%), m.p. 147° C. (recrystallised from ethyl acetate).

NMR Spectrum (CDCl$_3$, δ values) 1.83-2.03 (m, 4H), 2.98 (s, 3H), 3.76 (s, 3H), 3.77-3.98 (m, 4H), 5.11 (s, 2H), 6.62 (m, 1H), 6.73 (m, 1H), 6.74 (d, 1H), 6.83 (t, 1H), 7.38-7.43 (m, 1H), 7.59-7.65 (m, 2H), 7.67 (d, 1H).

The 6-bromomethyl-1-methyl-1,2-dihydroquinolin-2-one, used as a starting material immediately above, was obtained as follows (the reaction was repeated to give the necessary amount of starting material):

A mixture of 1,2-dihydro-1,6-dimethylquinolin-2-one (4.4 g; *Helv. Chim. Acta.*, 1970, 53, 1903), N-bromosuccinimide (4.53 g), azobisisobutyronitrile (0.01 g) and carbon tetrachloride (75 ml) was heated to reflux for 3 hours. The mixture was evaporated and the residue was partitioned between ethyl acetate and water. The organic phase was washed with water, dried (MgSO$_4$) and evaporated. The residue was purified by column chromatography using a 2:1 v/v mixture of toluene and ethyl acetate as eluent. There was thus obtained the required starting material (4.8 g, 75%), as a solid, m.p. 107°-108° C. *NMR Spectrum* (CDCl$_3$, δ values ) 3.7 (s, 3H), 4.57 (s, 2H), 6.7-7.5 (d, 1H), 7.25-7.65 (m, 4H).

4-(5-Fluoro-3-hydroxyphenyl)-4-methoxytetrahydropyran used as a starting material above was obtained as follows (the reaction steps were repeated to give the necessary amount of starting material):

Sodium hydride (50% w/w dispersion in mineral oil, 12.4 g) was added portionwise to a mixture of benzyl alcohol (26.7 ml) and DMA (500 ml) and the mixture was stirred at ambient temperature for 1 hour. 1-Bromo-3,5-difluorobenzene (50 g) was added carefully to control the vigour of the ensuing exothermic reaction. The mixture was stirred at ambient temperature for 2 hours and the solvent was evaporated. The residue was partitioned between methylene chloride and water and the organic phase was washed with water (4×50 ml), dried (MgSO$_4$) and evaporated. The residue was purified by distillation to give 3-benzyloxy-1-bromo-5-fluorobenzene (41.8 g, 57%), as a colourless liquid (b.p. 124°-130° C. at 0.3 mm Hg).

A solution of a portion (9.75 g) of this product in THF (150 ml) was cooled to −75° C. and n-butyl-lithium (1.6M in hexane, 22 ml) was added dropwise. The mixture was stirred at −75° C. for 1 hour and a solution of tetrahydropyran-4-one (3.47 g) in THF (10 ml) was added dropwise. The mixture was stirred at −75° C. for 1 hour and then allowed to warm to 0° C. A saturated aqueous ammonium chloride solution (50 ml) was added and the organic phase was separated, dried (MgSO$_4$) and evaporated. The residue was purified by column chromatography using a 1:1 v/v mixture of toluene and ethyl acetate as eluent. There was thus obtained 4-(3-benzyloxy-5-fluorophenyl)-4-hydroxytetrahydropyran (7.4 g, 71%) as an oil.

After appropriate repetition of the above-mentioned reaction the product so obtained (12.1 g) was dissolved in THF (150 ml) and sodium hydride (50% w/w dispersion in mineral oil, 2.11 g) was added portionwise. The mixture was stirred at ambient temperature for 1 hour, cooled in an ice-bath and methyl iodide (3.75 ml) was added dropwise. The mixture was stirred at ambient temperature for 18 hours, 2N aqueous hydrochloric acid (3 drops) were added and the organic solvent was evaporated. The residue was partitioned between ethyl acetate and water. The organic phase was separated, washed with water and with brine, dried (MgSO$_4$) and evaporated. There was thus obtained 4-(3-benzyloxy-5-fluorophenyl)-4-methoxytetrahydropyran (12.5 g, 99%), as a pale yellow oil which was used without further purification.

A solution of the product so obtained in ethanol (100 ml) was hydrogenated in the presence of 10% palladium-on-charcoal catalyst for 3 hours. The mixture was filtered and the filtrate was evaporated. There was thus obtained 4-(5-fluoro-3-hydroxyphenyl)-4-methoxytetrahydropyran (7.7 g, 86%), m.p. 123°-124° C.

EXAMPLE 2

Using the procedure described in Example 1, except that the reaction mixture was heated to 90° C. for 2 hours, 4-[5-fluoro-3-(1-methyl-2-oxo-1,2,3,4-tetrahydroquinolin-6-ylmethoxy)phenyl]-4-methoxytetrahydropyran was reacted with Lawesson's Reagent to give 4-[5-fluoro-3-(1-methyl-2-thioxo-1,2,3,4-tetrahydroquinolin-6-ylmethoxy)phenyl]-4-methoxytetrahydropyran in 28% yield, m.p. 136°-138° C.

The 4-[5-fluoro-3-(1-methyl-2-oxo-1,2,3,4-tetrahydroquinolin-6-ylmethoxy)phenyl]-4-methoxytetrahydropyran used as a starting material was obtained as follows:

A mixture of 4-[5-fluoro-3-(1-methyl-2-oxo-1,2-dihydroquinolin-6-ylmethoxy)phenyl]-4-methoxytetrahydropyran (0.628 g), platinum oxide (0.19 g), ethyl acetate (20 ml) and ethanol (20 ml) was stirred under 5 atmospheres pressure of hydrogen for 8 hours. The mixture was filtered and the filtrate was evaporated. The residue was purified by column chromatography using initially a 9:1 v/v mixture of methylene chloride and diethyl ether and then a 7:3 v/v mixture of the same solvents as eluent. There was thus obtained an oil which crystallised on trituration under diethyl ether to give the required starting material (0.325 g, 51%), m.p. 133° C.

EXAMPLE 3

Using the procedure described in Example 1 except that the reaction mixture was heated to reflux for 15 minutes, 4-[5-fluoro-3-(1-methyl-2-oxo-1,2,3,4-tetrahydroquinolin-6-ylthio)phenyl]-4-methoxytetrahydropyran was reacted with Lawesson's Reagent to give 4-[5-fluoro-3-(1-methyl-2-thioxo-1,2,3,4-tetrahydroquinolin-6-ylthio)phenyl]-4-methoxytetrahydropyran in 85% yield, m.p. 133.6°–134.2° C.

The 4-[5-fluoro-3-(1-methyl-2-oxo-1,2,3,4-tetrahydroquinolin-6-ylthio)phenyl]-4-methoxytetrahydropyran used as a starting material was obtained as follows:

Butyl-lithium (1.4M in hexane, 1.43 ml) was added dropwise to a mixture of 6-mercapto-1-methyl-1,2,3,4-tetrahydroquinolin-2-one (0.386 g), 4-(3,5-difluorophenyl)-4-methoxytetrahydropyran (0.547 g) and N-methylpyrrolidin-2-one (6 ml) which had been cooled in an ice-bath. The mixture was stirred and allowed to warm to ambient temperature. The mixture was heated to 145° C. for 2 hours, the hexane being distilled out of the reaction mixture. The mixture was cooled to ambient temperature and partitioned between ethyl acetate and water. The organic phase was washed with water and with N aqueous sodium hydroxide solution, dried (MgSO$_4$) and evaporated. The residue was purified by column chromatography using increasingly polar mixtures of methylene chloride and diethyl ether as eluent. There was thus obtained the required starting material (0.404 g, 50%) m.p. 124°–125° C.

The 6-mercapto-1-methyl-1,2,3,4-tetrahydroquinolin-2-one used in the preparation of the starting material above was obtained as follows:

A mixture of 1-methyl-1,2-dihydroquinolin-2-one (8 g), 10% palladium-on-charcoal catalyst (2 g) and ethanol (60 ml) was stirred under a pressure of 3.5 atmospheres of hydrogen for 24 hours. The mixture was filtered and evaporated. The residue was purified by column chromatography using a 9:1 v/v mixture of methylene chloride and diethyl ether as eluent. There was thus obtained 1-methyl-1,2,3,4-tetrahydroquinolin-2-one (7.88 g, 98%) as an oil.

A portion (1.6 g) of the product so obtained was added dropwise to chlorsulphonic acid (8 ml) and the mixture was heated to 80° C. for 2.5 hours. The mixture was cooled to ambient temperature, poured onto a mixture of ice and water and extracted with ethyl acetate. The organic phase was washed with water, dried (MgSO$_4$) and evaporated to give 1-methyl-2-oxo-1,2,3,4-tetrahydroquinolin-6-ylsulphonyl chloride (1.97 g, 76%), m.p. 137°–139° C.

NMR Spectrum (CDCl$_3$, δ values) 2.7–3.25 (m, 4H), 3.41 (s, 3H), 7.13 (d, 1H), 7.80–8.10 (m, 2H).

Triethylsilyl iodide (5 g) was added dropwise to a solution of a portion (1.2 g) of the product so obtained in methylene chloride (40 ml) and the mixture was stirred at ambient temperature for 16 hours. The mixture was washed with a saturated aqueous sodium bicarbonate solution and with a saturated aqueous sodium sulphite solution, dried (MgSO$_4$) and evaporated. The residue was purified by column chromatography using a 9:1 v/v mixture of methylene chloride and diethyl ether as eluent. There was thus obtained di-(1-methyl-2-oxo-1,2,3,4-tetrahydroquinolin-6-yl) disulphide (0.418 g, 43%), m.p. 130° C.

NMR Spectrum (CD$_3$COCD$_3$, δ values) 2.40–3.0 (m, 4H), 3.26 (s, 3H), 6.84 (d, 1H), 7.15–7.40 (m, 2H).

After repetition of the preceding steps, triphenylphosphine (0.432 g), water (2.5 ml) and concentrated hydrochloric acid (1 drop) were added in turn to a suspension of the disulphide (0.576 g) in 1,4-dioxane (5 ml). The mixture was stirred at ambient temperature for 1 hour. The mixture was partitioned between ethyl acetate and water. The organic phase was washed with water and with brine, dried (MgSO$_4$) and evaporated. The residual oil crystallised on trituration in a mixture of petroleum ether (b.p. 60°–80° C.) and diethyl ether.

There was thus obtained 6-mercapto-1-methyl-1,2,3,4-tetrahydroquinolin-2-one (0.456 g, 80%), m.p. 84° C.

The 4-(3,5-difluorophenyl)-4-methoxytetrahydropyran used in the preparation of the starting material above was obtained as follows:

A Grignard reagent was prepared from 3,5-difluorobromobenzene (38.6 g) and magnesium (4.88 g) in a mixture of toluene (100 ml) and THF (50 ml) using the following method. The 3,5-difluorobromobenzene was dissolved in toluene (50 ml) and a portion (approx. 5%) of the solution was added to a stirred suspension of the magnesium in a mixture of toluene (50 ml) and THF (50 ml). The mixture was stirred at ambient temperature for approximately 40 minutes until the initiation of the exothermic formation of the Grignard reagent was observed. The mixture was cooled in an ice-bath to a temperature in the range 15° to 20° C. while the remainder of the solution of 3,5-difluorobromobenzene was added. The mixture was stirred at ambient temperature for 2 hours.

Tetrahydropyran-4-one (10.69 g) was added over 1 hour to a portion (100 ml) of the Grignard reagent so obtained which was cooled to a temperature in the range 15° to 20° C. The mixture was stirred at ambient temperature for 2 hours. The mixture was cooled in an ice-bath and aqueous hydrochloric acid solution (50% w/v, 25 ml) and brine (30% w/v, 52 ml) were added in turn. The toluene layer was separated and the aqueous layer was extracted with toluene (32 ml). The organic solutions were combined and washed with water (4×32 ml). The solution was evaporated under reduced pressure to a volume of 16.3 ml. There was thus obtained a concentrated (90% w/v) solution of 4-(3,5-difluorophenyl)-4-hydroxytetrahydropyran in toluene. The concentrate was warmed to 60° C. and chlorobenzene (22.25 ml) was added, the temperature being maintained at 60° C. The mixture was allowed to cool to ambient tmeperature and then cooled in an ice-bath to a temperature in the range 0° to 5° C. The precipitate was isolated and washed with hexane (2×10 ml). There was thus obtained 4-(3,5-difluorophenyl)-4-hydroxytetrahydropyran (12.2 g).

A portion (7.15 g) of the material so obtained was dissolved in N-methylpyrrolidin-2-one (25 ml) and added to a slurry of sodium hydride (60% w/w dispersion in mineral oil; 3.34 g) in N-methylpyrrolidin-2-one (32 ml) which was cooled in an ice-bath to approximately 20° C. The mixture was stirred at this temperature for 30 minutes. Methyl iodide (5.22 g) was dissolved in N-methylpyrrolidin-2-one (2 ml) and added to the mixture. The resultant mixture was warmed to 30° C. and stirred for 2 hours. The mixture was evaporated. There was thus obtained 4-(3,5-difluorophenyl-4- methoxytetrahydropyran which was used without further purification.

EXAMPLE 4

The following illustrate representative pharmaceutical dosage forms containing the compound of formula I, or a pharmaceutically-acceptable salt thereof (hereafter compound X), for therapeutic or prophylactic use in humans:

| (a) Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |
| (b) Tablet II | mg/tablet |
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |
| (c) Tablet III | mg/tablet |
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |
| (d) Capsule | mg/capsule |
| Compound X | 10 |
| Lactose Ph.Eur | 488.5 |
| Magnesium stearate | 1.5 |
| (e) Injection I | (50 mg/ml) |
| Compound X | 5.0% w/v |
| 1M Sodium hydroxide solution | 15.0% v/v |
| 0.1M Hydrochloric acid (to adjust pH to 7.6) | |
| Polyethylene glycol 400 | 4.5% w/v |
| Water for injection to 100% | |
| (f) Injection II | (10 mg/ml) |
| Compound X | 1.0% w/v |
| Sodium phosphate BP | 3.6% w/v |
| 0.1M Sodium hydroxide solution | 15.0% v/v |
| Water for injection to 100% | |
| (g) Injection III | (1 mg/ml, buffered to pH6) |
| Compound X | 0.1% w/v |
| Sodium phosphate BP | 2.26% w/v |
| Citric acid | 0.38% w/v |
| Polyethylene glycol 400 | 3.5% w/v |
| Water for injection to 100% | |
| (h) Aerosol I | mg/ml |
| Compound X | 10.0 |
| Sorbitan trioleate | 13.5 |
| Trichlorofluoromethane | 910.0 |
| Dichlorodifluoromethane | 490.0 |
| (i) Aerosol II | mg/ml |
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |
| (j) Aerosol III | mg/ml |
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |
| (k) Aerosol IV | mg/ml |
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

Note
The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

CHEMICAL FORMULAE $$Q-A^1-X^1-Ar-\underset{R^3}{\underset{|}{\overset{OR^1}{\overset{|}{C}}}}-R^2 \qquad I$$

$$Z-Ar-\underset{R^3}{\underset{|}{\overset{OR^1}{\overset{|}{C}}}}-R^2 \qquad II$$

$$H-X^1-Ar-\underset{R^3}{\underset{|}{\overset{OR^1}{\overset{|}{C}}}}-R^2 \qquad III$$

$$Q-A^1-X^1-Ar-\underset{R^3}{\underset{|}{\overset{OH}{\overset{|}{C}}}}-R^2 \qquad IV$$

$$Q-A^1-X^1-Ar-\underset{R^3}{\underset{|}{\overset{OH}{\overset{|}{C}}}}-A^3-X^2-H \qquad V$$

SCHEME 1

$$Z-Ar-CHO \quad Z-Ar-CN \quad Z-Ar-CO_2R$$

$$\downarrow (i) \quad \downarrow (i) \quad \swarrow (i)$$

$$Z-Ar-\underset{R^3}{\overset{OR}{\overset{}{CH}}} \xrightarrow{(ii)} Z-Ar-CO-R^3$$

$$\downarrow (iii)$$

$$Z-Ar-Z \xrightarrow{(iv)} Z-Ar-\underset{R^3}{\underset{|}{\overset{OH}{\overset{|}{C}}}}-R^2 \xrightarrow{(v)}$$

$$Z-Ar-\underset{R^3}{\underset{|}{\overset{OR^1}{\overset{|}{C}}}}-R^2$$

II

Reagents
(i) R$^3$Li or R$^3$MgZ, THF
(ii) DDQ or MnO$_2$
(iii) R$^2$Li or R$^2$MgZ, THF;
(iv) BuLi or Mg, THF; R$^2$COR$^3$, THF
(v) R$^1$Z, base Note
R = (1–4C)alkyl such as Me or Et

SCHEME II

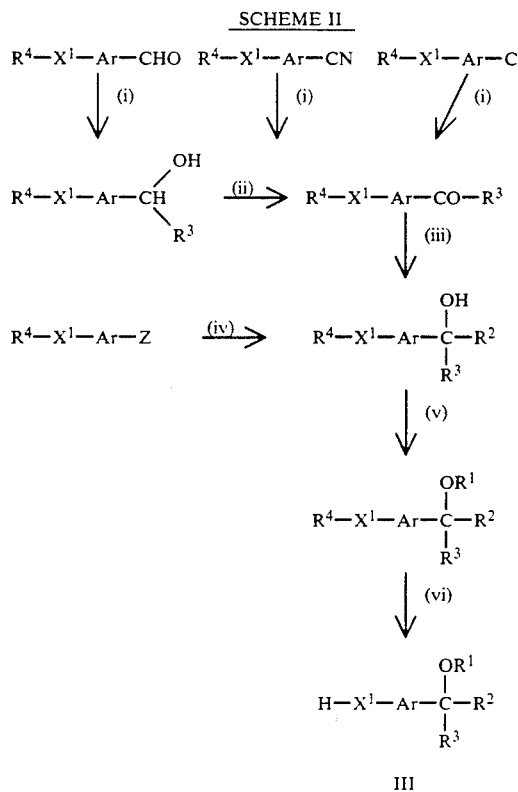

Reagents
(i) to (v) as in Scheme I
(vi) Conventional removal of the protecting group $R^4$ which is, e.g. COMe, THP, CH$_2$Ph or Me.

SCHEME III

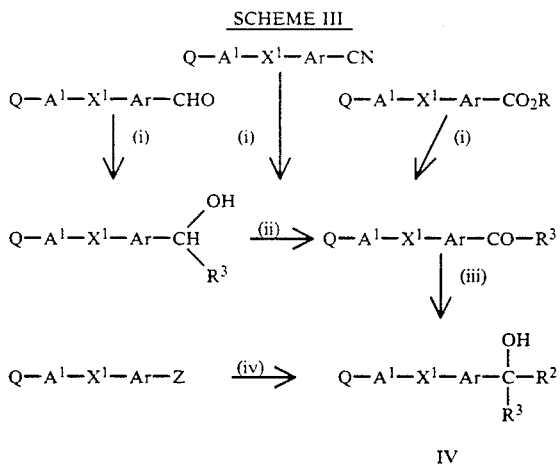

Reagents
(i) to (iv) as in Scheme I

SCHEME IV

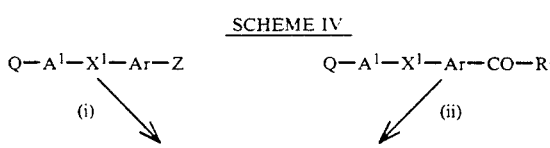

-continued
SCHEME IV

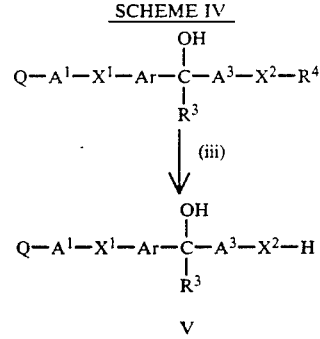

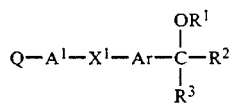

Reagents
(i) BuLi or Mg, THF; $R^3$—CO—$A^3$—$X^2$—$R^4$
(ii) $R^4$—$X^2$—$A^3$—Li or $R^4$—$X^2$—$A^3$—MgZ, THF
(iii) Conventional removal of the protecting group $R^4$ which is, e.g. COMe, THP, CH$_2$Ph or Me.

What we claim is:
1. A thioxo heterocycle of the formula I

$$Q-A^1-X^1-Ar-\underset{R^3}{\overset{OR^1}{\underset{|}{\overset{|}{C}}}}-R^2 \qquad I$$

wherein Q is quinolinyl, or a hydrogenated quinolinyl, which bears one or two thioxo substituents, and which may optionally bear one, two or three further substituents selected from halogeno, hydroxy, cyano, amino, (1–4C)alkyl, (1–4C)alkoxy, fluoro-(1–4C)alkyl, (1–4C)alkylamino, di-[(1–4C)alkyl]amino, amino-(1–4C)alkyl, (1–4C)alkylamino-(1–4C)alkyl, di[(1–4C)alkyl]amino-(1–4C)alkyl, phenyl and phenyl-(1–4C)alkyl, and wherein said phenyl or phenyl-(1–4C)alkyl substituent may optionally bear a substituent selected from halogeno, (1–4C)alkyl and (1–4C)alkoxy;
wherein $A^1$ is a direct link to $X^1$ or is (1–3C)alkylene;
wherein $X^1$ is oxy, thio, sulphinyl, sulphonyl or imino;
wherein Ar is phenylene which may optionally bear one or two substituents selected from halogeno, hydroxy, amino, nitro, cyano, carbamoyl, ureido, (1–4C)alkyl, (1–4C)alkoxy, (1–4C)alkylamino, di-[(1–4C)alkyl]amino, fluoro-(1–4C)alkyl and (2–4C)alkanoylamino; or Ar is pyridylene;
wherein $R^1$ is (1–4C)alkyl, (3–4C)alkenyl or (3–4C)alkynyl; and
wherein $R^2$ and $R^3$ together form a group of the formula —$A^2$—$X^2$—$A^3$— which, together with the carbon atom to which $A^2$ and $A^3$ are attached, defines a ring having 5 to 7 ring atoms, wherein $A^2$ and $A^3$, which may be the same or different, each is (1–3C)alkylene and $X^2$ is oxy, thio, sulphinyl or sulphonyl, and which ring may bear one, two or three substituents, which may be the same or different, selected from hydroxy, (1–4C)alkyl and (1–4C)alkoxy;
or wherein $R^1$ and $R^2$ together form a group of the formula —$A^2$—$X^2$—$A^3$— which, together with the oxygen atom to which $A^2$ is attached and with the carbon atom to which $A^3$ is attached, defines a ring having 5 to 7 ring atoms, wherein $A^2$ and $A^3$, which may be the same or different, each is (1–3C)alkylene and $X^2$ is oxy, thio, sulphinyl or sulphonyl, and which ring may bear one, two or three (1–4C)alkyl substituents, and wherein $R^3$ is (1–4C)alkyl, (2–4C)alkenyl or (2–4C)alkynyl; or a pharmaceutically-acceptable salt thereof.

2. A thioxo heterocycle of the formula I as claimed in claim 1 wherein Q is 2-thioxo-1,2-dihydroquinolinyl or 2-thioxo-1,2,3,4-tetrahydroquinolinyl which may optionally bear one, two or three substituents selected from fluoro, chloro, bromo, hydroxy, cyano, amino, methyl, ethyl, propyl, methoxy, trifluoromethyl, 2-fluoroethyl, 2,2,2-trifluoroethyl, 2-methylaminoethyl, 2-dimethylaminoethyl, phenyl and benzyl, and wherein said phenyl or benzyl substituent may optionally bear a substituent selected from chloro, methyl and methoxy;

$A^1$ is a direct link to $X^1$ or is methylene;

$X^1$ is oxy, thio, sulphinyl or sulphonyl;

Ar is 1,3-phenylene or 1,4-phenylene which may optionally bear one or two substituents selected from fluoro, chloro, hydroxy, amino, nitro, ureido, methoxy, dimethylamino, trifluoromethyl and acetamido; or Ar is 3,5-pyridylene;

$R^1$ is methyl, ethyl, allyl or 2-propynyl; and $R^2$ and $R^3$ together form a group of the formula $-A^2-X^2-A^3-$ which, together with the carbon atom to which $A^2$ and $A^3$ are attached, defines a ring having 5 or 6 ring atoms, wherein $A^2$ is ethylene, $A^3$ is methylene or ethylene, and $X^2$ is oxy, and which ring may bear one or two substituents selected from methyl, ethyl, propyl, methoxy and ethoxy;

or $R^1$ and $R^2$ together form a group of the formula $-A^2-X^2-A^3-$ which, together with the oxygen atom to which $A^2$ is attached and with the carbon atom to which $A^3$ is attached, defines a ring having 5 or 6 ring atoms, wherein $A^2$ is methylene, $A^3$ is methylene or ethylene, and $X^2$ is oxy, and which ring may bear one, two or three substituents selected from methyl, ethyl and propyl, and $R^3$ is methyl or ethyl; or a pharmaceutically acceptable salt thereof.

3. A thioxo heterocycle of the formula I as claimed in claim 1 wherein Q is 2-thioxo-1,2-dihydroquinolin-6-yl or 2-thioxo-1,2,3,4-tetrahydroquinolin-6-yl which may optionally bear one substituent selected from methyl and ethyl;

$A^1$ is a direct link to $X^1$, or is methylene;

$X^1$ is oxy, thio, sulphinyl or sulphonyl;

Ar is 1,3-phenylene which may optionally bear one or two substituents selected from fluoro, methoxy and trifluoromethyl;

$R^1$ is methyl, ethyl, or allyl; and $R^2$ and $R^3$ together form a group of the formula $-A^2-X^2-A^3-$ which, together with the carbon atom to which $A^2$ and $A^3$ are attached, defines a ring having 5 or 6 ring atoms, wherein $A^2$ is ethylene, $A^3$ is methylene or ethylene and $X^2$ is oxy, and which ring may bear a substituent selected from methyl, ethyl, propyl and methoxy;

or a pharmaceutically-acceptable salt thereof.

4. A thioxo heterocycle of the formula I as claimed in claim 1 wherein Q is 1-methyl-2-thioxo-1,2-dihydroquinolin-6-yl or 1-methyl-2-thioxo-1,2,3,4-tetrahydroquinolin-6-yl;

$A^1$ is methylene; $X^1$ is oxy;

Ar is 1,3-phenylene or 5-fluoro-1,3-phenylene;

$R^1$ is methyl; and $R^2$ and $R^3$ together form a group of the formula $-A^2-X^2-A^3-$ which, together with the carbon atom to which $A^2$ and $A^3$ are attached, defines a ring having 6 ring atoms, wherein each of $A^2$ and $A^3$ is ethylene and $X^2$ is oxy, and which ring may bear a methyl or ethyl substituent alpha to $X^2$;

or a pharmaceutically-acceptable salt thereof.

5. A thioxo heterocycle of the formula I as claimed in claim 1 wherein Q is 1-methyl-2-thioxo-1,2-dihydroquinolin-6-yl or 1-methyl-2-thioxo-1,2,3,4-tetrahydroquinolin-6-yl;

$A^1$ is methylene and $X^1$ is oxy, or $A^1$ is a direct link to $X^1$ and $X^1$ is thio;

Ar is 1,3-phenylene or 5-fluoro-1,3-phenylene;

$R^1$ is methyl; and $R^2$ and $R^3$ together form a group of the formula $-A^2-X^2-A^3-$ which, together with the carbon atom to which $A^2$ and $A^3$ are attached, defines a ring having 6 ring atoms, wherein each of $A^2$ and $A^3$ is ethylene and $X^2$ is oxy, and which ring may bear a methyl or ethyl substituent alpha to $X^2$;

or a pharmaceutically-acceptable salt thereof.

6. A thioxo heterocycle of the formula I, or a pharmaceutically-acceptable salt thereof as defined in claim 1, selected from 4-[5-fluoro-3-(1-methyl-2-thioxo-1,2-dihydroquinolin-6-ylmethoxy)phenyl]-4-methoxytetrahydropyran and 4-[5-fluoro-3-(1-methyl-2-thioxo-1,2,3,4-tetrahydroquinolin-6-ylmethoxy)phenyl]-4-methoxytetrahydropyran.

7. The thioxo heterocycle of the formula I, or a pharmaceutically-acceptable salt thereof as defined in claim 1 being 4-[5-fluoro-3-(1-methyl-2-thioxo-1,2,3,4-tetrahydroquinolin-6-ylthio)phenyl]-4-methoxytetrahydropyran.

8. A pharmaceutical composition which comprises a thioxo heterocycle of the formula I, or a pharmaceutically-acceptable salt thereof, as claimed in any one of claims 1–7 and 11 in association with a pharmaceutically-acceptable diluent or carrier.

9. A method of treating inflammatory and allergic diseases mediated alone or in part by one or more leukotrienes which comprises administering to a warm-blooded animal requiring such treatment an effective amount of a thioxo heterocycle of the formula I, or a pharmaceutically-acceptable salt thereof, as claimed in any one of claims 1–7.

* * * * *